US00PP23048P2

(12) United States Plant Patent
Hofmann

(10) Patent No.: US PP23,048 P2
(45) Date of Patent: Sep. 18, 2012

(54) ***IBERIS* PLANT NAMED 'IB2401'**

(50) Latin Name: *Iberis hybrida*
Varietal Denomination: IB2401

(75) Inventor: Silvia Hofmann, Mainz (DE)

(73) Assignee: Innovaplant GmbH + Co. KG, Gensingen (DE)

( * ) Notice: Subject to any disclaimer, the term of this patent is extended or adjusted under 35 U.S.C. 154(b) by 296 days.

(21) Appl. No.: 12/802,238

(22) Filed: Jun. 1, 2010

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

U.S. PATENT DOCUMENTS

PP22,280 P2 * 11/2011 Richards ..... Plt./263.1

OTHER PUBLICATIONS

UPOV ROM GTITM Computer Database, GTI Jouve Retrieval Software 2011/04 Citation for 'IB2401'.*

Anonymous. *Iberis* Absolutely Amethyst™ ('IB2401' PPAF CPBRAF) available at http://www.waltersgardens.com/plants/General-Perennia1/2139_Iberis-ABSOLUTELY-AMETHYST.*

* cited by examiner

*Primary Examiner* — Wendy C Haas
(74) *Attorney, Agent, or Firm* — C. A. Whealy

(57) ABSTRACT

A new and distinct cultivar of *Iberis* plant named 'IB2401', characterized by its compact, upright, outwardly spreading and mounding plant habit; vigorous growth habit; freely branching habit; dense and bushy habit; and dark violet-colored flowers.

1 Drawing Sheet

Botanical designation: *Iberis hybrida*.
Cultivar denomination: 'IB2401'.

BACKGROUND OF THE INVENTION

The present invention relates to a new and distinct cultivar of *Iberis* plant, botanically known as *Iberis hybrida* and hereinafter referred to by the name 'IB2401'.

The new *Iberis* plant is a product of a planned breeding program conducted by the Inventor in Gensingen, Germany. The objective of the breeding program is to create new freely branching *Iberis* plants with unique flower colors.

The new *Iberis* plant originated from a cross-pollination made by the Inventor during the spring of 2004 in Gensingen, Germany of two unidentified selections of *Iberis hybrida*, not patented. The new *Iberis* plant was discovered and selected by the Inventor as a single flowering plant from within the progeny of the stated cross-pollination in a controlled environment in Gensingen, Germany in 2005.

Asexual reproduction of the new *Iberis* plant by terminal cuttings in a controlled environment in Gensingen, Germany since 2006, has shown that the unique features of this new *Iberis* plant are stable and reproduced true to type in successive generations.

SUMMARY OF THE INVENTION

Plants of the new *Iberis* have not been observed under all possible environmental conditions. The phenotype may vary somewhat with variations in environmental conditions such as temperature and light intensity without, however, any variance in genotype.

The following traits have been repeatedly observed and are determined to be the unique characteristics of 'IB2401'.

These characteristics in combination distinguish 'IB2401' as a new and distinct *Iberis* plant:

1. Compact, upright, outwardly spreading and mounding plant habit.
2. Vigorous growth habit.
3. Freely branching habit; dense and bushy habit.
4. Dark violet-colored flowers.

Plants of the new *Iberis* differ from plants of the parent selections primarily in the following characteristics:

1. Plants of the new *Iberis* are more freely branching than plants of the parent selections.
2. Plants of the new *Iberis* and the parent selections differ in flower color.

Plants of the new *Iberis* can be compared to plants of *Iberis sempervirens* 'White Lace', not patented. In side-by-side comparisons conducted in Gensingen, Germany, plants of the new *Iberis* differed from plants of 'White Lace' in the following characteristics:

1. Plants of the new *Iberis* flowered later than plants of 'White Lace'.
2. Plants of the new *Iberis* and 'White Lace' differed in flower color as plants of 'White Lace' had white-colored flowers.

Plants of the new *Iberis* can also be compared to plants of *Iberis sempervirens* 'Alexander's White', not patented. In side-by-side comparisons conducted in Gensingen, Germany, plants of the new *Iberis* differed from plants of 'Alexander's White' in the following characteristics:

1. Plants of the new *Iberis* flowered later than plants of 'Alexander's White'.
2. Plants of the new *Iberis* and 'Alexander's White' differed in flower color as plants of 'Alexander's White' had white-colored flowers.

BRIEF DESCRIPTION OF THE PHOTOGRAPHS

The accompanying colored photographs illustrate the overall appearance of the new *Iberis* plant showing the colors as true as it is reasonably possible to obtain in colored reproductions of this type. Colors in the photographs may differ slightly from the color values cited in the detailed botanical description which accurately describe the colors of the new *Iberis* plant.

The photograph at the bottom of the sheet comprises a side perspective view of a typical flowering plant of 'IB2401' grown in a container.

The photograph at the top of the sheet is a close-up view of a typical flowering plant of 'IB2401'.

DETAILED BOTANICAL DESCRIPTION

Plants used for the aforementioned photographs and following description were grown under conditions which closely approximate commercial production conditions during the spring in 20-cm containers in an outdoor nursery in Bonsall, Calif. During the production of the plants, day temperatures averaged 29° C. and night temperatures averaged 4° C. Plants were pinched one time and were 14 months old when the photographs and description were taken. In the following description, color references are made to The Royal Horticultural Society Colour Chart, 2007 Edition, except where general terms of ordinary dictionary significance are used.

Botanical classification: *Iberis hybrida* 'IB2401'.

Parentage:

*Female, or seed, parent*.—Unidentified selection of *Iberis hybrida*, not patented.

*Male, or pollen, parent*.—Unidentified selection of *Iberis hybrida*, not patented.

Propagation:

*Type*.—By terminal cuttings.

*Time to initiate roots, summer and winter*.—About 10 to 14 days at 24° C.

*Time to produce a rooted young plant, summer*.—About three weeks at 24° C.

*Time to produce a rooted young plant, winter*.—About three to four weeks at 24° C.

*Root description*.—Medium in thickness, fibrous; white in color.

*Rooting habit*.—Freely branching; moderately dense.

Plant description:

*Plant and growth habit*.—Perennial; compact, upright, outwardly spreading and mounding plant habit; vigorous growth habit; freely branching habit; about nine primary branches develop per plant each with about six to eight secondary laterals; dense and bushy habit.

*Plant height*.—About 16 cm.

*Plant diameter*.—About 35 cm.

Lateral branch description:

*Length*.—About 18 cm.

*Diameter*.—About 6 mm.

*Internode length*.—About 3.5 cm.

*Strength*.—Strong.

*Aspect: Upright to outwardly spreading.*

*Texture, young*.—Smooth, glabrous.

*Texture, older*.—Woody.

*Color, young*.—Close to 146C.

*Color, older*.—Close to 199B.

Foliage description:

*Arrangement*.—Alternate, simple; sessile.

*Length*.—About 4.2 cm.

*Width*.—About 8 mm.

*Shape*.—Narrowly spatulate.

*Apex*.—Broadly acute.

*Base*.—Attenuate; slightly decurrent.

*Margin*.—Entire.

*Texture, upper and lower surfaces*.—Smooth, glabrous; tough, leathery.

*Venation pattern*.—Parallel.

*Color*.—Developing leaves, upper and lower surfaces: Close to 146B. Fully expanded leaves, upper and lower surfaces: Close to 147A; venation, close to 147B.

Flower description:

*Flower arrangement and habit*.—Small, asymmetrical cruciferous flowers arranged in short terminal racemes; flowers develop acropetally towards the apex; flowers face outwardly to upright; freely flowering habit with about 65 flowers per inflorescence.

*Fragrance*.—None detected.

*Natural flowering season*.—Plants flower during the spring in California.

*Flower longevity*.—Flowers last about five to seven days on the plant; flowers not persistent.

*Inflorescence height*.—About 4.7 cm.

*Inflorescence diameter*.—About 3.3 cm.

*Flower width*.—About 7 mm to 11 mm.

*Flower length*.—About 1.1 cm.

*Flower depth*.—About 9 mm.

*Flower buds*.—Length: About 6 mm. Diameter: About 3 mm. Shape: Oval. Color: Close to N87D.

*Petals*.—Arrangement: Four petals; two smaller upper petals and two larger lower petals. Shape: Obovate. Apex: Rounded. Base: Acute. Margin: Entire. Length: Upper petals: About 6 mm. Lower petals: About 1 cm. Width: Upper petals: About 3 mm. Lower petals: About 5 mm. Texture, upper and lower surfaces: Smooth, glabrous. Color: When opening, upper and lower surfaces: Close to NN155D tinted irregularly with close to N87D. Fully opened, upper surface: Close to 83B; color becoming closer to 83D with development. Fully opened, lower surface: Centers and towards the base, close to NN155D; towards the margins and apex, tinted with close to N87B to N87D.

*Sepals*.—Arrangement: Calyx cup-shaped with four sepals in a single whorl. Length: About 3 mm. Width: About 2 mm. Shape: Elliptical. Apex: Acute. Base: Truncate. Margin: Entire. Texture, upper and lower surfaces: Smooth, glabrous. Color, upper surface: Close to 194B. Color, lower surface: Close to 146D.

*Peduncles*.—Length: About 2 cm. Diameter: About 2.5 mm. Angle: Mostly upright. Strength: Strong. Texture: Smooth, glabrous; longitudinal ridges. Color: Close to 146B.

*Pedicels*.—Length: About 6 mm. Diameter: About 1 mm. Angle: Erect to 90° from peduncle axis. Strength: Strong. Texture: Sparsely pubescent. Color: Close to 146B.

*Reproductive organs*.—Stamens: Quantity/arrangement: Six per flower. Filament length: About 1.5 mm. Filament color: Close to 145C. Anther shape: Ligulate. Anther length: About 1 mm. Anther color: Close to N144A. Pollen amount: Scarce. Pollen color: Close to 160D. Pistils: Quantity: One per flower. Pistil length: About 6 mm. Style length: About 2.5 mm. Style color: Close to N187B. Stigma shape: Rounded. Stigma color: Close to 195B. Ovary color: Close to 146C; towards the apex, tinted with close to 187A.

*Seed/fruit*.—Seed and fruit development have not been observed on plants of the new *Iberis*.

Pathogen/pest resistance: Plants of the new *Iberis* have not been observed to be resistant to pests and pathogens common to *Iberis* plants.

Garden performance: Plants of the new *Iberis* have been observed to have good garden performance and to tolerate wind and rain. Plants of the new *Iberis* are hardy to USDA Hardiness Zone 4.

It is claimed:

1. A new and distinct *Iberis* plant named 'IB2401' as illustrated and described.

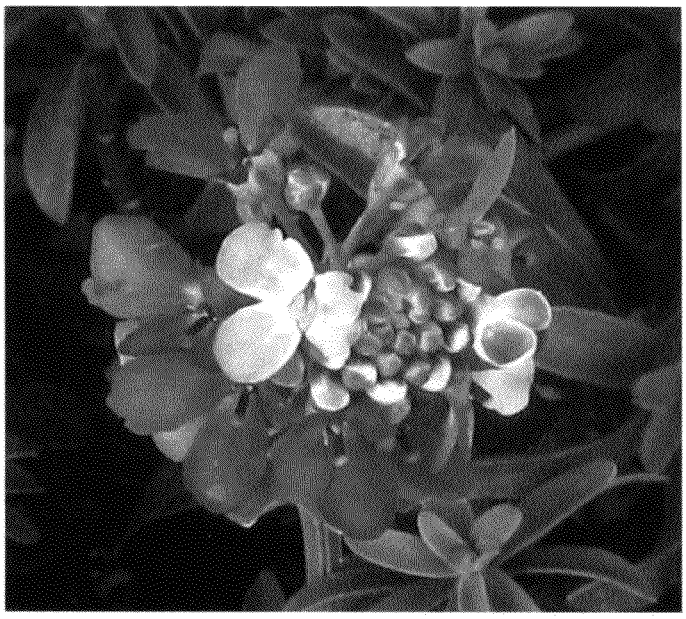
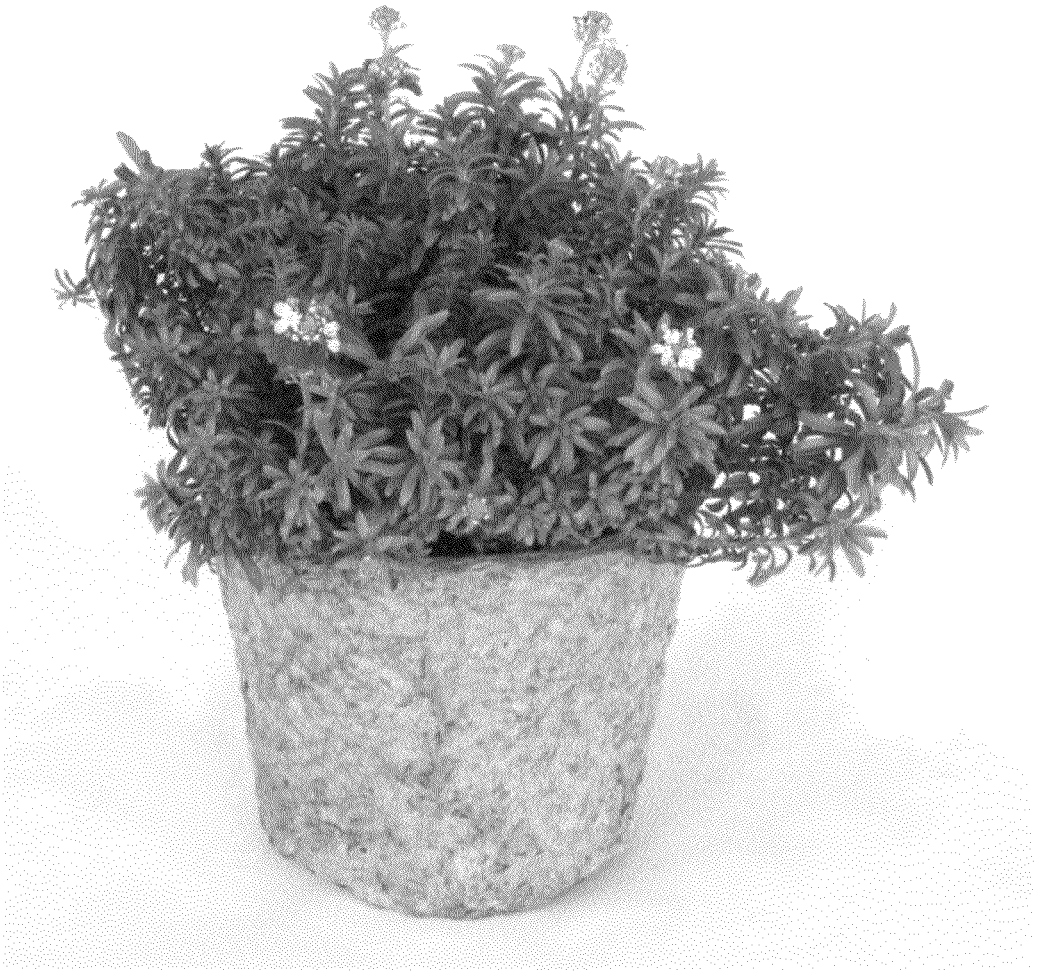

* * * * *